United States Patent [19]
Müller et al.

[11] Patent Number: 5,610,399
[45] Date of Patent: Mar. 11, 1997

[54] APPARATUS AND PROCESS FOR THE SPATIALLY RESOLVED OPTICAL DETERMINATION OF DENSITY DISTRIBUTIONS IN BIOLOGICAL TISSUES

[75] Inventors: Gerhard Müller; Jürgen Beuthan; Olaf Minet, all of Berlin; Michael Kaschke, Oberkochen, all of Germany

[73] Assignee: Carl-Zeiss-Stiftung, Heidenheim, Germany

[21] Appl. No.: 284,507

[22] PCT Filed: Dec. 4, 1993

[86] PCT No.: PCT/EP93/03408

§ 371 Date: Sep. 6, 1994

§ 102(e) Date: Sep. 6, 1994

[87] PCT Pub. No.: WO94/13194

PCT Pub. Date: Jun. 23, 1994

[30] Foreign Application Priority Data

Dec. 9, 1992 [DE] Germany .......................... 42 41 416.4
Dec. 11, 1992 [DE] Germany .......................... 42 41 772.4

[51] Int. Cl.$^6$ ............................................. G01N 21/49
[52] U.S. Cl. ............................................. 250/341.1
[58] Field of Search ............................... 250/341.1

[56] References Cited

U.S. PATENT DOCUMENTS

| | | | |
|---|---|---|---|
| 4,515,165 | 5/1985 | Carroll | 128/664 |
| 4,948,974 | 8/1990 | Nelson et al. | 250/358.1 |
| 5,148,022 | 9/1992 | Kawaguchi et al. | 250/339.06 |

*Primary Examiner*—Constantine Hannaher

[57] ABSTRACT

A process for the optical spatially resolved determination of density distributions in biological tissues includes as a first step irradiating a biological tissue by directing a locally confined beam of electromagnetic radiation at an incidence position of the tissue; keeping the incidence position fixed; determining the thickness of the tissue being irradiated; and sensing and recording the directly transmitted radiation component and the scattered radiation component in a spatially resolved manner over a defined spatial angle. As a second step, the incidence position is changed and the first step is repeated. As a third step, the second step is repeated a number of times to obtain a reconstructive representation of the tissue through which the radiation has passed, based on the spatially resolved recordings of the transmitted and scattered radiation components and the tissue thickness as determined in each repetition of the first step.

4 Claims, 1 Drawing Sheet

APPARATUS AND PROCESS FOR THE SPATIALLY RESOLVED OPTICAL DETERMINATION OF DENSITY DISTRIBUTIONS IN BIOLOGICAL TISSUES

The present invention relates to an apparatus and a process for the spatially resolving optical determination of density distributions in biological tissues.

A series of apparatuses or processes have long been known for the imaging investigation of human tissues. Thus, for example, X-rays are used in order to obtain images of the human skeletal structure with good contrast. In the detection of tumors, where the density differences to be detected between the different tissue constituents are in some cases smaller than 5%, the image quality which can attained in this fashion is however often insufficient for a reliable diagnosis. The use of X-rays is moreover disadvantageous in that they have an ionizing effect on the irradiated body parts.

NMR spectroscopic in vivo investigations are also known and offer only limited possibilities of evaluation in the case of such small optical density differences in the tissue. Moreover, such processes are expensive and require long measurement times.

Therefore, for the imaging diagnosis of biological tissues, optical processes which are to avoid the known disadvantages of X-ray or NMR spectroscopic investigation processes have been sought for a considerable time. Such apparatuses or processes on an optical basis are described, for example, in U.S. Pat. No. 4,972,331. It is furthermore known from the publication by J. M. Schmitt et al., "Use of polarized light to discriminate shortpath photons in a multiply scattering medium" (Applied Optics, Vol. 31, No. 30, pp. 6353–6546) how the detection of "foreign bodies" in strongly scattering media can be effected by means of infrared irradiation and in particular by the evaluation of the components of the scattered radiation.

However, the optically based apparatuses or processes from the said publications have in common the disadvantage that only qualitative statements can be made concerning the presence of certain tissue components, e.g., tumors. Thus it is however not possible to localize such tissue components precisely in the tissue or to exactly determine their dimensions.

The object of the present invention is therefore to provide a process for eliminating the above mentioned disadvantages of the prior art. The process of the present invention comprises as a first step irradiating a biological tissue by directing a locally confined beam of electromagnetic radiation at an incidence position of the tissue, keeping the incidence position fixed, determining the thickness of the tissue being irradiated, and sensing and recording the directly transmitted radiation component and the scattered radiation components in a spatially resolved manner over a defined spatial angle. The process further comprises, as a second step, changing the incidence position of the beam of electromagnetic radiation and repeating the first step. Additionally, the process comprises as a third step repeating the second step a number of times to obtain a reconstructive representation of the tissue through which the radiation has passed, based on the spatially resolved recordings of the transmitted and scattered radiation components and the tissue thickness determined in each repetition of the first step.

The use, according to the invention, of a scanning unit which makes possible both the defined positioning of a locally confined beam of radiation from a radiation source and also the simultaneous spatially resolved recording of the transmitted radiation components now makes possible the highly precise, spatially resolved determination of density distributions or density changes in biological tissues. Thus, for example, precise statements can be made concerning the localization in human tissues of tumors which have different optical densities in comparison with the surrounding healthy tissue. Likewise exact information is now accessible concerning the dimensions of such altered density distributions.

Besides the primarily desired spatially resolving detection of local density changes in the tissue, the apparatus according to the invention can however also be used to sense small density changes in the tissue over long periods. This can be required, for example, for the monitoring of tissue changes in the course of a pharmacological treatment. An evaluation of the recorded signals can then take place, for example, in a manner such as that described in the publication of J. M. Schmitt et al., cited hereinabove.

Differently constructed scanning units can be used in the apparatus according to the invention, according to the desired evaluation. In all, a modular construction is possible of the whole apparatus, in which the individual components are interchangeable according to the use.

Further advantages, and also details of the apparatus according to the invention and also of a process for its operation, will become apparent from the following description of embodiment examples with reference to the accompanying Figures.

Figure 1:
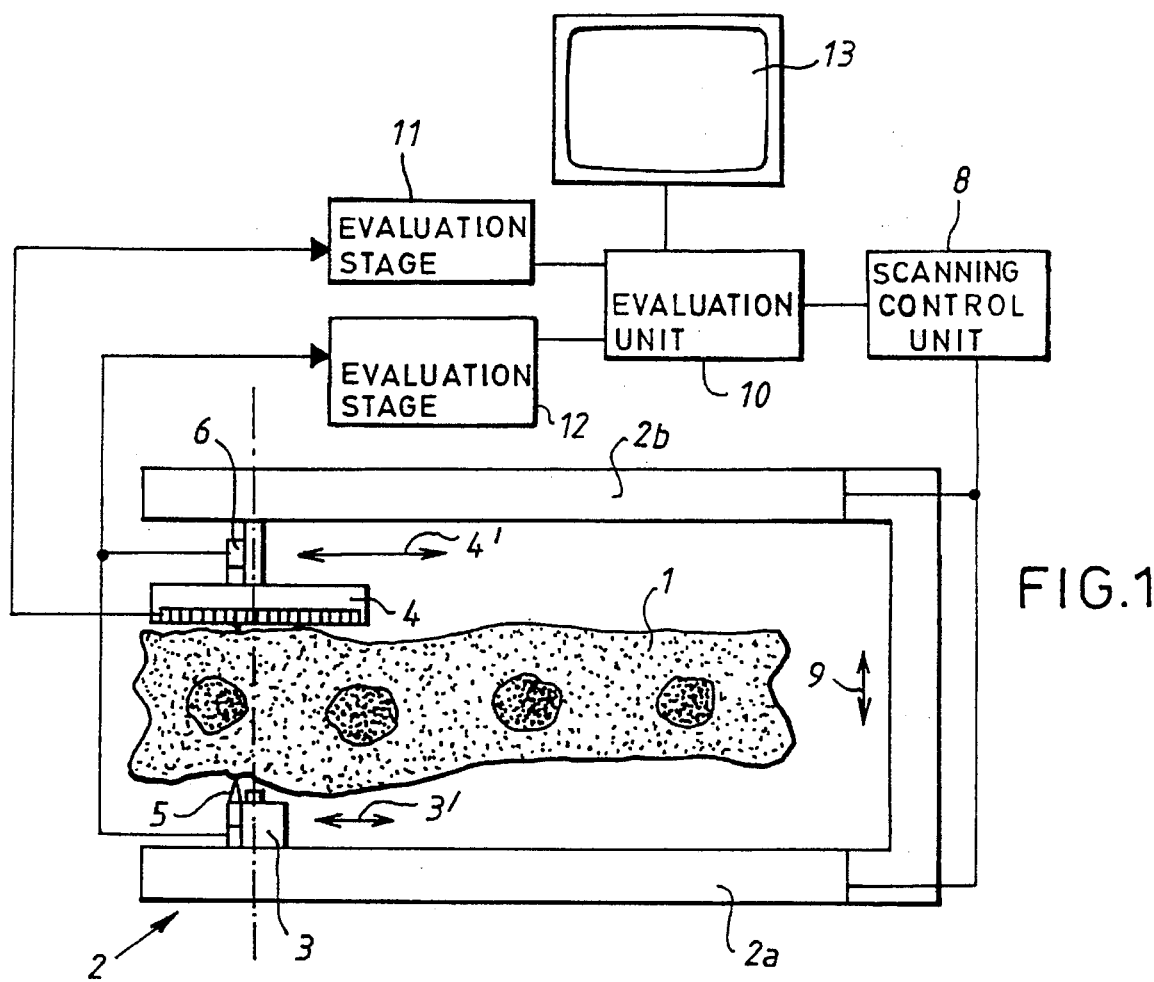
FIG. 1 shows a first embodiment example of the apparatus according to the invention, in a schematic representation.

A first embodiment example of the apparatus according to the invention will be described with reference to FIG. 1. The biological tissue (1) to be investigated, e.g., a part of the human hand, is here arranged between the jaws (2a, 2b) of a U-shaped measuring frame (2) in which the scanning unit is integrated. The distance between the two jaws (2a, 2b) of the measuring frame (2) is adjustable in a defined manner, as schematically illustrated by the arrow with the reference numeral (9). This can be effected by means of a known displacement mechanism or the like. The displacement mechanism furthermore includes a length measuring device, likewise not shown, in the form of a known incremental or absolute path measurement system, which makes possible, for evaluation purposes, a continuous sensing of the present adjusted distance of the two jaws (2a, 2b).

The measuring frame is furthermore advantageously made disinfectable, by a suitable choice of material. It has thus been found to be favorable for the measuring frame, including the scanning unit, to be constructionally designed such that they are easily dismantled and that the individual parts can be easily sterilized in an autoclave.

Besides the radiation source (3), the detector unit (4) and the respective associated displacement device of the radiation source (3) and detector unit (4), the scanning unit proper also contains a thickness measuring device (5, 6) with which the respective present thickness of the tissue (1) to be investigated is sensed.

According to the invention, the radiation source (3) is arranged on one of the two jaws (2a) of the measuring frame (2), and the detector unit (4) is arranged on the opposing jaw (2b). Both the radiation source (3) and the detector unit (4) can be positioned in a defined manner in a plane by means of the displacement device (not shown), as indicated by the two arrows (3') and (4'). It is thus possible to effect displacement along a straight line and also a displacement in a plane. A scanning unit control (8) undertakes the defined displacement of the radiation source (3) and detector unit (4), according to the desired scan mode, and also senses the respective present positions of the radiation source (3) and detector unit (4).

Other than the illustrated possibility of designing both the radiation source (3) and the detector unit (4) as displaceable in a defined manner, an alternative possibility is to displace either only the radiation source or only the detector unit. Likewise, a detector unit can be used of which, for example, the sensitivity can be locally changed in a timed sequence during a scanning process.

At any given time, it is only important that, at a known position of the place at which the radiation is incident on the tissue, there takes place on the output side a spatially dependent recording of the transmitted or scattered radiation components.

According to the invention, a spatially resolved sensing of the transmitted and scattered radiation components takes place over a given spatial angle by means of the detector unit (4) in a first scanning process, with the incidence position of the radiation source (3) kept fixed. In the subsequent scanning processes, the position at which the radiation from the radiation source (3) is incident is changed, by means of the scanning unit, relative to the tissue (1) through which the radiation is passed, and the scattered light distributions relating to this position of incidence are respectively sensed anew by means of the detector unit (4). Individual scanning processes are performed in this manner until, based on the recorded signals, a computer reconstruction is possible of the tissue through which the radiation has passed.

In the scanning processes subsequent to the first scanning process, simultaneously with the spatial variation of the place at which the radiation is incident, the respective detector unit can also be arranged to follow in step with it. A following action of this kind can appear, for example, such that the optical axes of the radiation source and detector unit are always moved synchronously with each other. There consequently results a pointwise irradiation of the tissue to be investigated, with simultaneous sensing of the transmitted scattered light distribution over a defined spatial angle. The position of the point light source relative to the tissue is incrementally changed in each successive scanning process.

A possible signal production can also take place, in addition to a simple measurement of the transmitted intensities, on the basis of phase modulation spectroscopy, as for example described in U.S. Pat. No. 4,972,331. Here the radiation amplitude is modulated on the transmission side at a radio frequency in the 100 MHz–500 MHz range, and the scattered radiation is recorded, spatially resolved, after passing through the tissue. The resulting phase changes of the radio frequency modulated light are then evaluated on the detector side, as are also the amplitude changes of the radio frequency component of the scattered radiation relative to the original radiation.

The further utilization in a suitable reconstruction process of the information produced is known, for example, from the publication by M. Schweiger, S. R. Arridge and D. T. Delpy, "Application of the Finite-Element Method for the Forward and Inverse Models in Optical Tomography", Journal of Mathematical Imaging and Vision, 3 (1993), p. 263.

One or more laser diodes act as the radiation source (3) in the illustrated embodiment example; they operate in the infrared spectral region, and can be radio frequency modulated according to the signal processing process. The laser diode, arranged with a corresponding optics in front of it, supplies a narrow well confined radiation beam, which can be scanned in a defined manner over the tissue (1) to be investigated, i.e., the radiation source can be considered as a point-like light source with a defined aperture and a defined aperture angle.

As an alternative, it is also possible, for example, to embody the desired light source with the narrowly confined radiation beam by means of a fiber optic light guide which is provided on the transmitting side, is arranged in front of a suitable radiation source, has its beam exit surface provided with a special collimating optics, and is moved or scanned over the tissue.

The deciding factor in the choice of the radiation source at any given time is that as narrowly limited as possible an aperture with a small aperture angle is present, and that the position of the incident radiation from it can be positioned in a defined manner relative to the tissue through which the radiation is to be passed.

Suitable radiation source wavelengths advantageously lie in the infrared spectral region between 600 nm and 1300 nm, where biological tissue has a relatively high transmission. As well as the use of a single wavelength, two or more wavelengths can also be used simultaneously in parallel. For this purpose, e.g., two or more radiation sources of different wavelengths can be correspondingly used.

A flat CCD array is provided on the receiver side as the detector unit (4) in the illustrated embodiment example; a spatially resolved recording of the transmitted and/or scattered radiation components is possible with it.

For operation with laser light modulated at radio frequency, the CCD array can likewise be selectively, directly modulated at a radio frequency or else can be operated with a preceding image amplifier with amplification modulated at a radio frequency. The modulation frequency on the detector side is then detuned by a frequency offset $\delta f$ in the kHz range relative to the modulation frequency of the laser diode, so that the CCD array records a signal, of a frequency $\delta f$, containing all the relevant information such as the amplitude and phase of the radio frequency modulated light.

The CCD array can then be positioned relative to the tissue (1) by means of the mentioned displacement device (not shown), as can the radiation source (3), so that even large tissue portions can be investigated thereby.

Alternatively, a CCD row can also be used as the detector unit (4), and can be correspondingly displaced. Besides this, the use is also possible on the detector side of a fiber optic light guide, followed by a wavelength-selective detector unit which records, in dependence on location, the radiation to be recorded, which has been transmitted or scattered in the tissue. For the spatially dependent recording of the scattered radiation components over a defined spatial angle, the inlet surface of the fiber optic light guide is scanned over the tissue on the exit side in a scanning process with the incident radiation position kept constant; this can likewise take place by means of a known displacement mechanism.

The methods described hereinabove for producing signals with radio frequency modulated light can of course also be used when a fiber optic sensor is used.

Besides the possibility, as in the illustrated embodiment example, of embodying both the radiation source (3) and the detector unit (4) to be variable in position in a defined manner, it can alternatively be arranged that only the radiation source (3) or only the detector unit (4) is correspondingly displaceable.

Besides a pure displacement, other scanning or raster processes can be used according to the invention, such as, for example, rotation around a cylinder-shaped tissue part or the like.

The scanning unit of the apparatus according to the invention furthermore includes a thickness measuring device (5, 6) by means of which the respective thickness of the tissue (1) through which radiation is at present passing can be determined. This information is necessary for evaluation—sketched hereinbelow—of the recorded radiation signals and the computer reconstruction of the tissue through which the radiation has passed. In the embodiment example of FIG. 1, in addition to the radiation source (3) and the detector unit (4), respective probe tips are arranged for thickness measurement, and press with a defined spring force against the tissue (1) through which radiation is to pass, thus being in direct contact with the boundary surfaces of the tissue. The output signals of the thickness measuring device (5, 6) are processed, together with the information relating to the distance which has been set between the two jaws (2a, 2b) of the measuring frame (2), in an associated evaluation stage (12) of the thickness measuring device (5, 6), which then delivers the determined thickness measurement values to the central evaluation unit (10) of the apparatus according to the invention.

As already indicated, the central evaluation unit (10) furthermore also processes the information which is sensed by the scanning unit control (8) concerning the present positions of the radiation source (3) and the detector unit (4). Finally, for the evaluation, the central evaluation unit (10) also requires the recorded signals of the amplitude and phase of the radio frequency modulated light, and also the constant light component, i.e., the non-modulated background, at the detector unit (4), which are passed to the central evaluation unit (10) by a suitable evaluation stage (11) of the detector unit (4).

The scattered light components, now according to the invention recorded spatially resolved for known radiation incidence position, can be used, with a known distance between the radiation source (3) and the detector unit (4), and also the known optical tissue parameters, to localize spatial "disturbances" in the investigated tissue Such "disturbances", such as tumors for example, have a different optical density in comparison with the surrounding healthy tissue, and can be localized with spatial resolution.

The reconstructive computation of the optical density distribution based on the information recovered in several scans takes place by unfolding algorithms with the use of computed forward kernels. Details of such an evaluation process can be found in the publication of M. Schweiger et al., already cited hereinabove.

The initial assumption here is that the scattering processes which take place in the tissue are correlated with the optical density distributions which are respectively present, and thus a reconstructive computation of the spatial density distributions present in the tissue is possible from the detection of the scattered light components. The unfolding of the recorded signals takes place with so-called adaptive forward kernels, which result from model computations based on the known scattering properties of the tissue to be investigated.

The object-dependent diffraction phenomena of the photon density waves can furthermore be made use of for the evaluation.

Finally, a two-dimensional or three-dimensional representation of the investigated tissue portions is possible from the completed reconstructive computation of the optical density distribution in the investigated tissue, by means of a succeeding image processing unit and a corresponding display (13).

Figure 2:
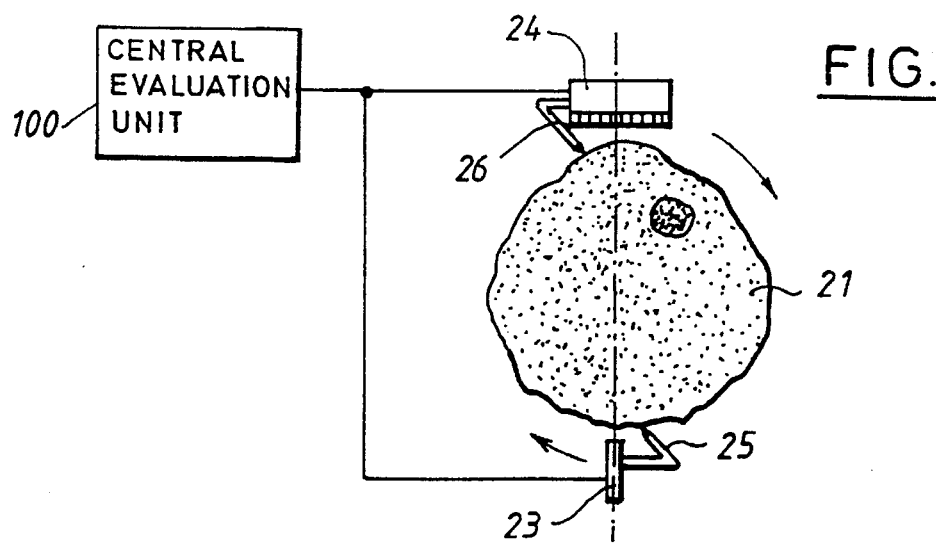
FIG. 2 shows a second embodiment example of the apparatus according to the invention, in a schematic representation.

An alternative form of embodiment of the apparatus according to the invention is shown in FIG. 2.

In contrast to the first embodiment example of FIG. 1, a tomographic gantry is provided instead of the measuring frame with integrated scanning unit, and the scanning unit is integrated into it. The radiation source (23) and the detector unit (24) of the scanning unit rotate in the fashion of a tomographic scanner around the tissue (21) to be investigated. The radiation source (23) is again designed here also as a point light source with a defined, small aperture. Moreover the detector unit (24), analogously to the first embodiment example, effects the spatially resolved recording of the transmitted radiation components.

Moreover the apparatus of this embodiment example according to the invention also includes a thickness measuring device (25, 26) in the form of two probe tips contacting the tissue (21).

The signal processing takes place in principle identically to that in the embodiment example described hereinabove, i.e., a central evaluation unit (100) is likewise provided which correspondingly processes the information of the scanning unit and of the thickness measuring device, and if necessary represents it on a display via an image processing unit.

By means of these embodiments of the apparatus according to the invention, sectional images, in particular, of the tissue to be investigated can be produced in very varied perspectives, such as are also obtained in the same manner in NMR tomography.

We claim:

1. Process for an optical, spatially resolved determination of density distributions in biological tissues, comprising:

a first step of irradiating a biological tissue by directing a locally confined beam of electromagnetic radiation at an incidence position of said tissue, keeping said incidence position fixed, determining a thickness of said tissue being irradiated, and sensing and recording a directly transmitted radiation component and scattered radiation components in a spatially resolved manner over a defined spatial angle, and a second step of changing said incidence position and repeating said first step, and a third step of repeating said second step a number of times to obtain a reconstructive representation of tissue through which said radiation has passed based on spatially resolved recordings of said transmitted and scattered radiation components and said tissue thickness as determined in each repetition of said first step.

2. Process according to claim 1, in which said beam of electromagnetic radiation is intensity-modulated at radio frequency, and relative changes of phase and amplitude of said scattered radiation components are recorded in a spatially dependent manner and evaluated.

3. Process according to claim 1, comprising using the object-dependent diffraction phenomena of photon density waves for the evaluation.

4. Apparatus for an optical, spatially resolved determination of density distributions in biological tissues, comprising:

a scanning unit having:

a radiation source for irradiating a biological tissue by directing a locally confined beam of electromagnetic radiation at a fixed incidence position of said tissue, a detector unit for sensing and recording a directly transmitted radiation component and scattered radiation components in a spatially resolved manner over a defined spatial angle during radiation at said fixed incidence position, a device for changing the incidence position of said locally confined beam of electromagnetic radiation, a thickness measuring devices for determining a thickness of said tissue to be irradiated, and an evaluation unit for providing a reconstructive representation of said tissue to be irradiated by said irradiation source, said evaluation unit being arranged to evaluate spatially resolved recordings of said transmitted and scattered radiation components recorded by said detector unit for a plurality of incidence positions and evaluating said tissue thicknesses as determined for a plurality of incidence positions by said thickness measuring device.

* * * * *